(12) United States Patent
Wada

(10) Patent No.: US 8,831,702 B2
(45) Date of Patent: Sep. 9, 2014

(54) BIO-SIGNAL DETECTION ELECTRODE AND BIO-SIGNAL DETECTION APPARATUS

(75) Inventor: Seiji Wada, Kanagawa (JP)

(73) Assignee: Sony Corporation, Tokyo (JP)

( * ) Notice: Subject to any disclaimer, the term of this patent is extended or adjusted under 35 U.S.C. 154(b) by 147 days.

(21) Appl. No.: 13/402,236

(22) Filed: Feb. 22, 2012

(65) Prior Publication Data

US 2012/0245451 A1   Sep. 27, 2012

(30) Foreign Application Priority Data

Mar. 23, 2011 (JP) ................................ 2011-063782

(51) Int. Cl.
*A61B 5/0478*  (2006.01)
*A61B 5/0496*  (2006.01)

(52) U.S. Cl.
USPC ............ 600/383; 600/396; 600/397; 607/153

(58) Field of Classification Search
CPC .. A61B 5/04087; A61B 5/0478; A61B 5/049; A61B 5/0492

USPC ............................ 600/396, 397, 383; 607/153
See application file for complete search history.

(56) References Cited

U.S. PATENT DOCUMENTS

| | | | | |
|---|---|---|---|---|
| 3,967,628 | A | * | 7/1976 | Vredenbregt ................. 607/149 |
| 3,998,213 | A | * | 12/1976 | Price .............................. 600/383 |
| 4,033,334 | A | * | 7/1977 | Fletcher et al. ............... 600/383 |
| 4,311,152 | A | * | 1/1982 | Modes et al. ................. 600/392 |
| 4,362,165 | A | * | 12/1982 | Carmon et al. ............... 600/396 |
| 4,633,879 | A | * | 1/1987 | Ong .............................. 600/391 |
| 5,782,761 | A | * | 7/1998 | Gusakov ....................... 600/391 |
| 6,510,333 | B1 | * | 1/2003 | Licata et al. .................. 600/383 |
| 2010/0125190 | A1 | * | 5/2010 | Fadem .......................... 600/383 |

FOREIGN PATENT DOCUMENTS

JP   2006-006666   1/2006

* cited by examiner

*Primary Examiner* — Lee S Cohen
(74) *Attorney, Agent, or Firm* — K&L Gates LLP

(57) ABSTRACT

Provided is a bio-signal detection electrode including: an electrode section made of a gel including an electrolytic solution; and a support section configured to support the electrode section with respect to an accessory, the electrode section adhering to the support section.

14 Claims, 4 Drawing Sheets

BIO-SIGNAL DETECTION ELECTRODE AND BIO-SIGNAL DETECTION APPARATUS

CROSS REFERENCES TO RELATED APPLICATIONS

The present application claims priority to Japanese Priority Patent Application JP 2011-063782 filed in the Japan Patent Office on Mar. 23, 2011, the entire content of which is hereby incorporated by reference.

BACKGROUND

The present disclosure relates to a bio-signal detection electrode used for measuring a bio-signal and to a bio-signal detection apparatus including the same.

Electrical signals (hereinafter, referred to as bio-signals) generated in a living body, particularly, a human body, include brain waves, an electrocardiogram, an electromyogram, and the like and, for measuring them, an electrode to be brought into contact with a measurement target site (skin, etc.) is used. As such an electrode, there are various electrodes depending on the states of measurement target sites and the kinds of bio-signals.

For example, Japanese Patent Application Laid-open No. 2006-006666 (FIG. 2) (hereinafter, referred to as Patent Document 1) discloses a brain wave detector including an electrode device for brain wave detection. The electrode device for brain wave detection includes a portion to be brought into contact with a scalp, the portion being made of an elastic member such a sponge or a non-woven fabric. This elastic member is impregnated with an electrolytic solution. In the brain wave detector, a plurality of such electrode devices for brain wave detection are arranged on a holding member having a cap shape or a helmet shape.

SUMMARY

The elastic members included in the electrode devices for brain wave detection disclosed in Patent Document 1 serve to adjust, when the holding member is put on the head of a subject, a distance between the holding member and the head depending on the shape of the head, which varies among individuals, and to ensure contacts of the electrode devices for brain wave detection with the scalp. Here, there is a fear that for example, when the subject moves his/her head, the brain wave detector is displaced (slidably shifted) on the head.

If the holding member is displaced, the electrode devices for brain wave detection supported by the holding member also move following the holding member. In this case, contact points of the electrode devices for brain wave detection, that is, measurement points of the brain waves are displaced. As a result, it becomes difficult to correctly measure the brain waves.

In view of the above-mentioned circumstances, there is a need to provide a bio-signal detection electrode and a bio-signal detection apparatus, which are capable of preventing influence on bio-signal measurement even if an accessory is displaced.

According to an embodiment of the present disclosure, there is provided a bio-signal detection electrode including an electrode section and a support section.

The electrode section is made of a gel including an electrolytic solution.

The support section is configured to support the electrode section with respect to an accessory, the electrode section adhering to the support section.

With this configuration, when the accessory is attached to a living body (animals including human beings), the electrode section is brought into contact with a surface of the living body and elastically deformed. An electrical signal (bio-signal) generated in the living body flows in the electrode section due to conduction through the electrolytic solution and is detected. If the accessory is displaced with respect to the living body, due to a frictional force between the electrode section and the surface of the living body, a tip of the electrode section is prevented from being moved from its contact position. The tip of the electrode section is elastically deformed following the support section while the electrode section keeps the contact position, and hence the support section receives an elastic force to a direction opposite to a direction in which the accessory is displaced. In other words, the accessory is returned to its original position before displacement due to restoration from the elastic deformation of the electrode section. Thus, the bio-signal detection electrode is capable of preventing influence on bio-signal measurement even if the accessory is displaced.

The support section may be made of a metal and include an adhering surface to which the electrode section adheres, the adhering surface being covered with a silver/silver chloride film.

In the case where the support section is made of a metal, there is a possibility that the metal constituting the support section is ionized due to a current of bio-signals and flows into the gel, which influences a detection potential. Here, the adhering surface to be brought into contact with the electrode section is covered with a silver/silver chloride film, and hence in the bio-signal detection electrode according to the embodiment of the present disclosure, it is possible to prevent the metal constituting the support section from being ionized.

The gel may be made of a material that melts at human body temperature.

With this configuration, in the case where the bio-signal detection electrode is used for a person, the electrode section melts at the human body temperature and a frictional force of the electrode section with respect to the human skin increases. Accordingly, even if the range in which the accessory is displaced is large, it is possible to prevent the electrode section from being detached from the human skin, that is, to extend the range of displacement of the accessory, within which the electrode section can be restored.

The support section may include the adhering surface formed to have a concavo-convex shape.

With this configuration, the adhering force of the electrode section with respect to the support section increases. Thus, even if the range in which the accessory is displaced is large, it is possible to prevent the electrode section from being detached from the support section, that is, to extend the range of displacement of the accessory, within which the electrode section can be restored.

According to another embodiment of the present disclosure, there is provided a bio-signal detection apparatus including an accessory and a bio-signal detection electrode.

The accessory is to be attached to a living body.

The bio-signal detection electrode includes an electrode section made of a gel including an electrolytic solution and a support section configured to support the electrode section with respect to the accessory, the electrode section adhering to the support section.

As described above, according to the present disclosure, it is possible to provide a bio-signal detection electrode and a bio-signal detection apparatus, which are capable of preventing influence on bio-signal measurement even if an accessory is displaced.

These and other objects, features and advantages of the present disclosure will become more apparent in light of the following detailed description of best mode embodiments thereof, as illustrated in the accompanying drawings. Additional features and advantages are described herein, and will be apparent from the following Detailed Description and the figures.

DETAILED DESCRIPTION

Hereinafter, an embodiment of the present disclosure will be described with reference to the drawings.
<Configuration of Bio-signal Detection Electrode>

Figure 1:
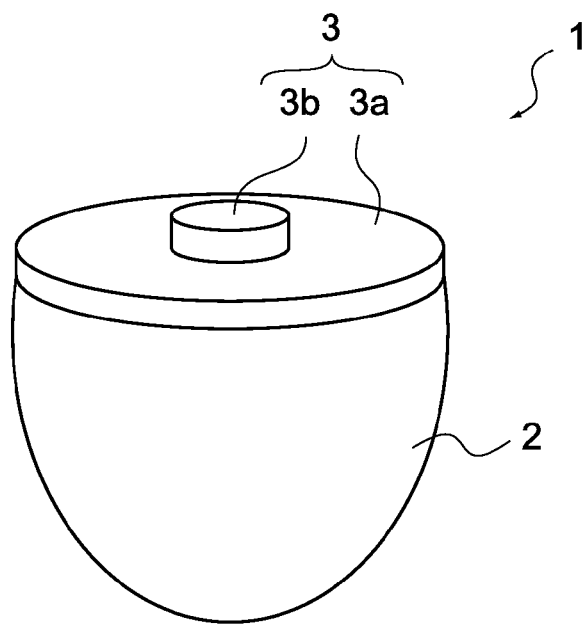
FIG. 1 is a perspective view of a bio-signal detection electrode according to an embodiment of the present disclosure.
Figure 2:
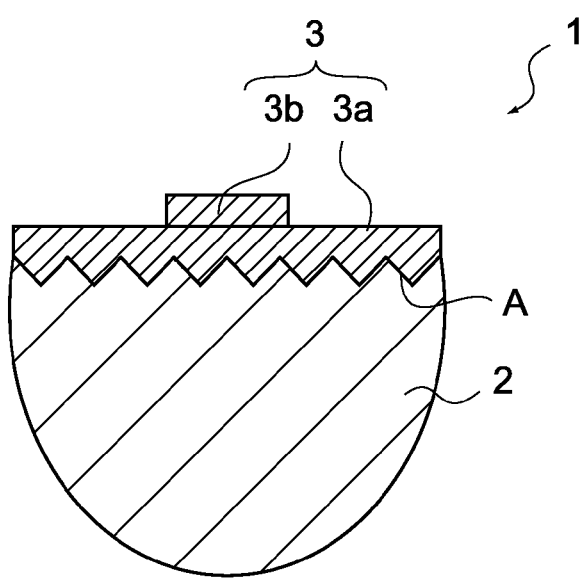
FIG. 2 is a cross-sectional view of the bio-signal detection electrode.

FIG. 1 is a perspective view of a bio-signal detection electrode 1 according to this embodiment. FIG. 2 is a cross-sectional view of the bio-signal detection electrode 1. As shown in those figures, the bio-signal detection electrode 1 includes an electrode section 2 and a support section 3. The electrode section 2 adheres to the support section 3.

The electrode section 2 is brought into contact with a skin (including scalp) of a living body and detects an electrical signal. The electrode section 2 is constituted of a gel including an electrolytic solution. The gel may be made of a coagulated gelatin, starch, or polymer. As the polymer, there are exemplified polysaccharide (glucomannan, agarose, etc.) and polyethyleneglycol. Alternatively, the gel may be made of a material in which a plurality of materials are mixed.

The constituent material of the gel is not limited and only needs to be able to hold the electrolytic solution and have a predetermined elasticity. Further, although will be described later, when the electrode section 2 is brought into contact with the living body, it is desirable that the electrode section 2 slightly melt at body temperature of a contact target site and therefore it is favorable that a material having such a property be used for the gel.

The electrolytic solution may be a metal chloride (KCl, NaCl, $MgCl_2$, etc.) solution. The electrolytic solution is not limited thereto and only needs to allow ionic conduction within the gel.

The electrode section 2 may be one gelled by impregnating the above-mentioned constituent material of the gel with the electrolytic solution. Alternatively, the electrode section 2 may be one gelled by solving salt of the above-mentioned metal chloride in a colloidal solvent with a gelatin or a starch being a colloid.

The shape of the electrode section 2 can be appropriately changed depending on the elasticity of the constituent material, the state of the contact target site (existence and absence of hair, etc.), and the like. In the bio-signal detection electrode 1 shown in FIG. 1, the electrode section 2 has a semi-oval shape. Other than this shape, the electrode section 2 may have a semi-spherical shape, a columnar shape, or the like. Alternatively, the electrode section 2 may have, for example, a shape such that its tip is separated like a brush.

The electrode section 2 can adhere to the support section 3 by gelling a liquid raw material held in contact with the support section 3. Alternatively, the electrode section 2 may adhere to the support section 3 by embedding the support section 3 in the gelled electrode section 2.

The support section 3 supports the electrode section 2 with respect to an accessory (which will be described later). The support section 3 may be constituted of a conductive material such as a metal or a carbon. The support section 3 includes a base portion 3a and a fixing portion 3b. To the base portion 3a, the electrode section 2 adheres. The fixing portion 3b serves to fix the support section 3 to the accessory. In the base portion 3a, a surface to which the electrode section 2 adheres is referred to as an adhering surface A.

The base portion 3a is a plate-like member having almost the same size as the electrode section 2 adhering thereto. In order to increase the adhering force of the electrode section 2, the adhering surface A may have a concavo-convex shape. The concavo-convex shape only needs to be a shape obtained by forming concavity and convexity in a flat surface. For example, the convexities may be formed in a stripe pattern, a grid pattern, or a dotted pattern.

In the case where the base portion 3a is made of a metal, the adhering surface A can be one that has been subjected to "anti-polarization processing." The anti-polarization processing is processing for preventing the metal constituting the base portion 3a from being ionized and flowing into the gel, which influences a detection potential.

The anti-polarization processing can be performed by covering a surface of the base portion 3a with a silver/silver chloride film. Specifically, the silver/silver chloride film can be formed on the adhering surface by plating.

It should be noted that the anti-polarization processing is effective in the case where the base portion 3a is constituted of a metal, but the anti-polarization processing is unnecessary in the case where the base portion 3a is constituted of a non-metallic conductive material (carbon, etc.).

The fixing portion 3b is, for example, a snap and fixes the support section 3 to the accessory. Other than this, the fixing portion 3b may be one fixed to the accessory by screwing or the like.

The bio-signal detection electrode 1 is configured as described above and mounted on the accessory such as a headband for use. In the following, a bio-signal detection apparatus with the bio-signal detection electrode 1 being mounted on the headband will be described. It should be noted that the headband is merely one example of the accessory and the headband may be replaced by another accessory attachable to the living body.
<Configuration of Bio-signal Detection Apparatus>

Figure 3:
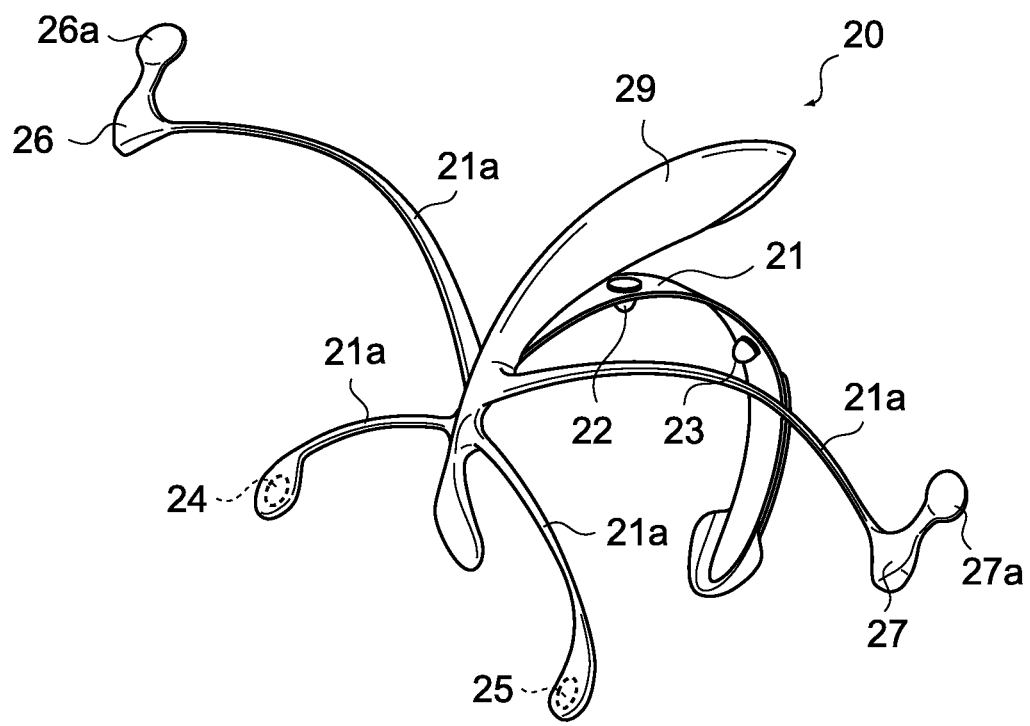
FIG. 3 is a perspective view of a bio-signal detection apparatus according to the embodiment of the present disclosure.

FIG. 3 is a perspective view showing a bio-signal detection apparatus 20. The bio-signal detection apparatus 20 is an apparatus for detecting brain waves (EEG: electroencephalogram) and eye motion (EOG: electrooculogram) of the user.

The bio-signal detection apparatus 20 includes a headband 21 to be put on the head of the user. The headband 21 is provided with an upper-head electrode 22, a posterior-head electrode 23, a right eye electrode 24, a left eye electrode 25, a right reference electrode 26, a left reference electrode 27, and a housing 29. As the upper-head electrode 22 and the posterior-head electrode 23, the bio-signal detection electrodes 1 can be used.

The headband 21 is a member covering the brow, the top, and then the back of the head of the user and is formed in a shape adapted for the head of the user, for example, a circular arc shape. The headband 21 has an elasticity and is supported on the head of the user due to the elasticity. In the headband 21, arms 21a are formed for supporting the right eye electrode 24, the left eye electrode 25, the right reference electrode 26, and the left reference electrode 27. It should be noted that the shape of the headband 21 can be appropriately changed.

The upper-head electrode 22 is an electrode to be brought into contact with the top of the head of the user. The posterior-head electrode 23 is an electrode to be brought into contact with the back of the head of the user. The upper-head electrode 22 and the posterior-head electrode 23 are electrodes for measuring brain waves of the user. A method of mounting the upper-head electrode 22 and the posterior-head electrode 23 on the headband 21 will be described later.

The right eye electrode 24 is an electrode to be brought into contact with the right temple of the user and may be a flat-plate-like electrode formed of a conductive material. The right eye electrode 24 is provided to the arm 21a extending from the headband 21 toward the right temple of the user.

The left eye electrode 25 is an electrode to be brought into contact with the left temple of the user and may be a flat-plate-like electrode formed of a conductive material, similarly. The left eye electrode 25 is provided to the arm 21a extending from the headband 21 toward the left temple of the user.

The right eye electrode 24 and the left eye electrode 25 are electrodes for measuring eye motion of the user.

The right reference electrode 26 is an electrode to be brought into contact with the back side of the lobe of the ear of the user and may be a flat-plate-like electrode formed of a conductive material. The right reference electrode 26 is provided to the arm 21a extending from the headband 21 toward the right ear of the user. The right reference electrode 26 is provided with an ear-lobe sandwiching portion 26a for sandwiching the lobe of the ear between the ear-lobe sandwiching portion 26a and the right reference electrode 26, the ear-lobe sandwiching portion 26a being turned to the front of the lobe of the ear.

The left reference electrode 27 is an electrode to be brought into contact with the lobe of the ear of the user and may be a flat-plate-like electrode formed of a conductive material. The left reference electrode 27 is provided to the arm 21a extending from the headband 21 toward the left ear of the user. The left reference electrode 27 is provided with an ear-lobe sandwiching portion 27a for sandwiching the lobe of the ear between the ear-lobe sandwiching portion 27a and the left reference electrode 27, the ear-lobe sandwiching portion 27a being turned to the front of the lobe of the ear.

The housing 29 is provided on the headband 21 so as not to be an obstacle to putting the headband 21 on the head of the user. The housing 29 houses electrical components such as a processor, a memory, and a communication interface.

<Method of Mounting Bio-signal Detection Electrode on Accessory>

Figure 4:
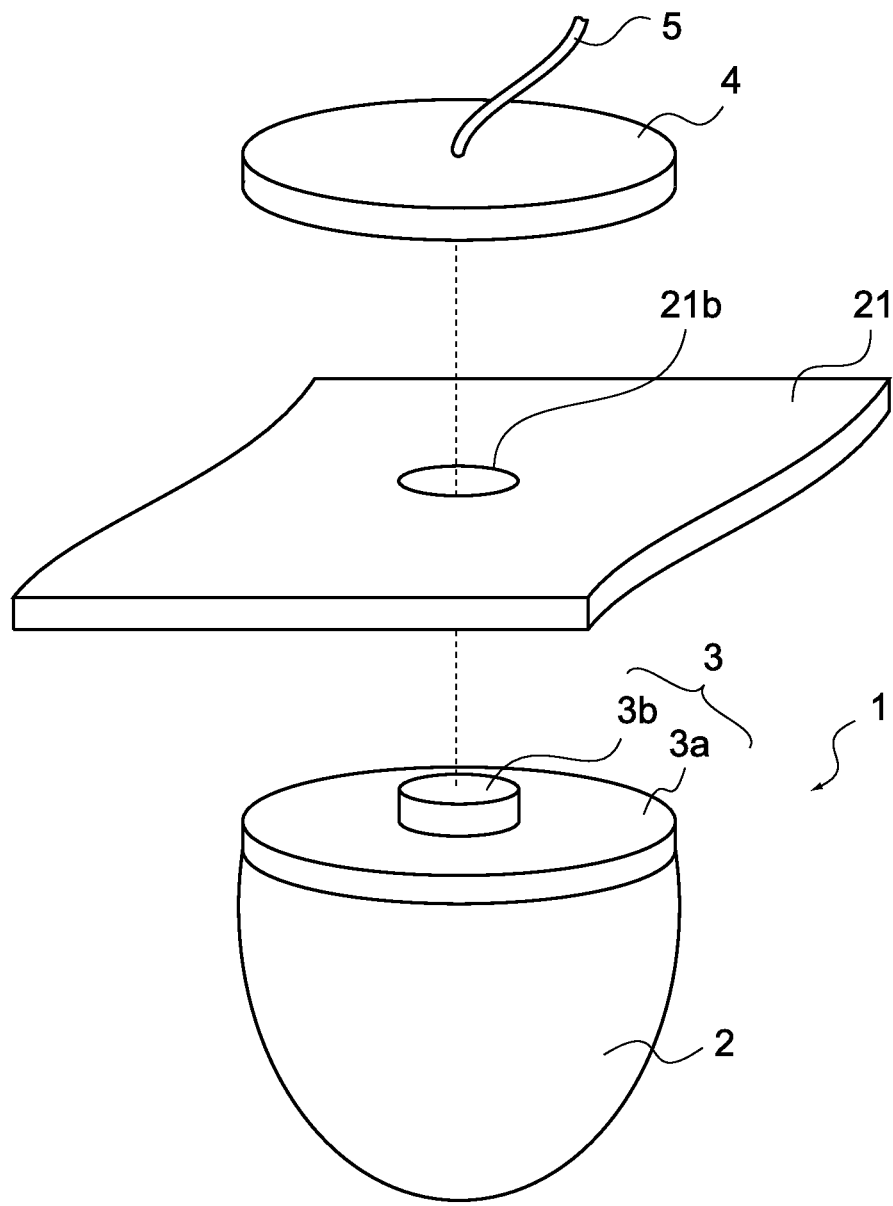
FIG. 4 is a schematic view showing a method of mounting the bio-signal detection electrode according to the embodiment of the present disclosure.

A method of mounting the upper-head electrode 22 and the posterior-head electrode 23 (i.e., bio-signal detection electrodes 1) on the headband 21 in the bio-signal detection apparatus 20 will be described. FIG. 4 is a schematic view showing a method of mounting the bio-signal detection electrode 1.

As shown in FIG. 4, the headband 21 is provided with a hole 21b corresponding to the size of the fixing portion 3b of the support section 3. The bio-signal detection electrode 1 is mounted on the headband 21 such that the fixing portion 3b is inserted into the hole 21b from the inside (side to be brought into contact with the head of the user) of the headband 21. Further, from the outside of the headband 21, a fitting member 4 capable of fitting to the fixing portion 3b is fitted to the fixing portion 3b. In this manner, the base portion 3a of the support section 3 and the fitting member 4 sandwich the headband 21 therebetween, and the bio-signal detection electrode 1 is mounted on the headband 21.

The fitting member 4 may be formed of a conductive material such as a metal. A bio-signal detected by the bio-signal detection electrode 1 is transmitted to the electrical components and the like via a signal line 5 connected to the fitting member 4. Such a method of mounting the bio-signal detection electrode 1 is merely one example and the bio-signal detection electrode 1 may be mounted on the headband 21 by a different method.

<Operation of Bio-signal Detection Electrode>

Operations of the bio-signal detection electrode 1 will be described. It is assumed that the bio-signal detection electrode 1 is mounted on the headband 21 of the above-mentioned bio-signal detection apparatus 20. FIG. 5 are schematic views showing the operations of the bio-signal detection electrode 1.

Figure 5A:
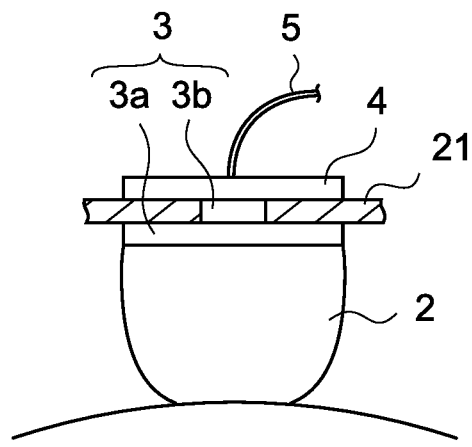
FIG. 5 are schematic views showing operations of the bio-signal detection electrode.

When the bio-signal detection apparatus 20 is put on the head of the user, as shown in FIG. 5A, the bio-signal detection electrode 1 is pressed against the scalp of the user by the headband 21 and the electrode section 2 is elastically deformed and brought into close contact with the scalp. Due to this elastic deformation, the electrolytic solution included in the electrode section 2 seeps between the electrode section 2 and the scalp, so that conductivity between the electrode section 2 and the scalp is maintained. Otherwise, in the case of using some constituent materials for the electrode section 2, the electrode section 2 slightly melts at body temperature of the user and brought into closer contact with the scalp.

Figure 5B:
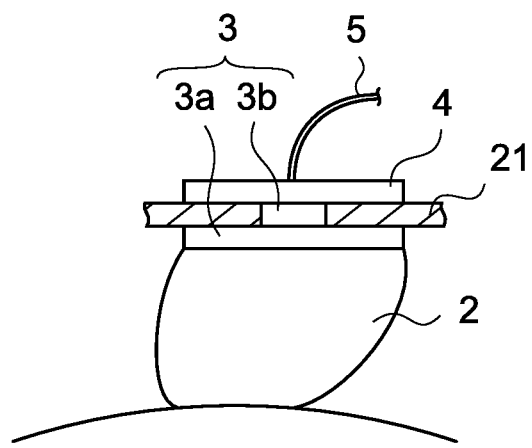

If the headband 21 is displaced with respect to the head of the user, as shown in FIG. 5B, due to a frictional force generated between the electrode section 2 and the scalp, the contact position of the electrode section 2 is kept and the electrode section 2 is elastically deformed to the displacement direction of the headband 21 following the movement of the headband 21. Thus, the headband 21 receives an elastic force in a direction opposite to the displacement direction from the electrode section 2 and is returned to its original position before displacement due to restoration from the elastic deformation of the electrode section 2.

As described above, even if the headband 21 is displaced, the bio-signal detection electrode 1 according to this embodiment can keep its contact position and correct the displacement of the accessory. Thus, it is possible to prevent influence on bio-signal measurement due to the displacement of the headband 21.

Further, in the case where the support section 3 is made of a metal, by covering the adhering surface A with a silver/silver chloride film, it is possible to prevent influence on a detection potential due to ionization of the metal constituting the support section 3.

In addition, by setting the gel constituting the electrode section 2 to be made of a material that slightly melts at human body temperature, it is possible to increase a frictional force of the electrode section 2 with respect to a human skin. With this, even if a range in which the headband 21 is displaced is large, it is possible to prevent the electrode section 2 from being detached from the contact position, that is, to extend the range of displacement of the headband 21, within which the electrode section 2 can be restored.

In addition, by forming the adhering surface of the support section 3 to have a concavo-convex shape, the adhering force of the electrode section 2 with respect to the support section 3 can be increased. With this, even if the range in which the headband 21 is displaced is large, it is possible to prevent the electrode section 2 from being detached from the support section 3, that is, to extend the range of displacement of the headband 21, within which the electrode section 2 can be restored.

The present disclosure is not limited only to this embodiment and can be modified without departing from the gist of the present disclosure.

It should be noted that the present disclosure can also be configured as follows.

(1) A bio-signal detection electrode, including:
an electrode section made of a gel including an electrolytic solution; and
a support section configured to support the electrode section with respect to an accessory, the electrode section adhering to the support section.

(2) The bio-signal detection electrode according to Item (1), in which the support section is made of a metal and includes an adhering surface to which the electrode section adheres, the adhering surface being covered with a silver/silver chloride film.

(3) The bio-signal detection electrode according to Item (1) or (2), in which the gel is made of a material that melts at human body temperature.

(4) The bio-signal detection electrode according to any one of Items (1) to (3),
in which the support section includes the adhering surface formed to have a concavo-convex shape.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed is:

1. A bio-signal detection electrode, comprising:
an electrode section made of a gel including an electrolytic solution, wherein the electrode section has a semi-spherical shape which is subject to change when the electrode section is attached to a living body; and
a support section configured to support the electrode section with respect to an accessory, wherein the support section includes a base portion including a conductive material and a fixing portion, and wherein the electrode section adheres to the base portion at an adhering surface, the adhering surface formed to have a plurality of concavo-convex surfaces to which the electrode section adheres.

2. The bio-signal detection electrode according to claim 1, wherein the base portion includes a metal and is covered with a silver/silver chloride film.

3. The bio-signal detection electrode according to claim 2, wherein the silver/silver chloride film is formed on the adhering surface.

4. The bio-signal detection electrode according to claim 1, wherein the gel includes a material that melts at human body temperature.

5. The bio-signal detection electrode according to claim 1, wherein the base portion includes a non-metallic conductive material.

6. The bio-signal detection electrode according to claim 1, wherein the gel includes at least one of coagulated gelatin, starch, and polymer.

7. A bio-signal detection apparatus, comprising:
an accessory to be attached to a living body; and
a bio-signal detection electrode including an electrode section made of a gel including an electrolytic solution, wherein the electrode section has a semi-spherical shape which is subject to change when the electrode section is attached to the living body, and
a support section configured to support the electrode section with respect to the accessory, wherein the support section includes a base portion including a conductive material and a fixing portion, and wherein the electrode section adheres to the base portion at an adhering surface, the adhering surface formed to have a plurality of concavo-convex surfaces to which the electrode section adheres.

8. The bio-signal detection apparatus according to claim 7, wherein the base portion includes a metal and is covered with a silver/silver chloride film.

9. The bio-signal detection apparatus according to claim 8, wherein the silver/silver chloride film is formed on the adhering surface.

10. The bio-signal detection apparatus according to claim 7, wherein the gel includes a material that melts at human body temperature.

11. The bio-signal detection apparatus according to claim 7, wherein the base portion includes a non-metallic conductive material.

12. The bio-signal detection apparatus according to claim 7, wherein the gel includes at least one of coagulated gelatin, starch, and polymer.

13. The bio-signal detection apparatus according to claim 7, wherein the accessory to be attached to a living body comprises a hole, and wherein the hole corresponds to a size of the fixing portion such that the fixing portion is configured to be inserted into the hole.

14. The bio-signal detection apparatus according to claim 13, further comprising a fitting member, wherein the fitting member and the base portion are configured to sandwich the accessory to be attached to a living body therebetween.

* * * * *